(12) United States Patent
Czygan et al.

(10) Patent No.: US 7,395,114 B2
(45) Date of Patent: Jul. 1, 2008

(54) INTRACARDIAL IMPEDANCE MEASURING ARRANGEMENT

(75) Inventors: Gerald Czygan, Buckenhof (DE); Michael Lippert, Ansbach (DE)

(73) Assignee: Biotronik GmbH & Co., Berlin (DE)

( * ) Notice: Subject to any disclaimer, the term of this patent is extended or adjusted under 35 U.S.C. 154(b) by 589 days.

(21) Appl. No.: 10/923,117

(22) Filed: Aug. 20, 2004

(65) Prior Publication Data

US 2005/0049646 A1   Mar. 3, 2005

(30) Foreign Application Priority Data

Sep. 1, 2003   (DE)   ................. 103 40 894
Dec. 16, 2003   (DE)   ................. 103 61 143

(51) Int. Cl.
*A61N 1/00*   (2006.01)

(52) U.S. Cl. .......................... 607/6; 600/509
(58) Field of Classification Search ............ 607/6, 607/8, 9
See application file for complete search history.

(56) References Cited

U.S. PATENT DOCUMENTS

| | | | |
|---|---|---|---|
| 4,919,136 A * | 4/1990 | Alt | 607/20 |
| 5,154,171 A | 10/1992 | Chirife | |
| 5,309,917 A * | 5/1994 | Wang et al. | 600/508 |
| 7,171,258 B2 * | 1/2007 | Goode | 600/509 |
| 2001/0012953 A1 | 8/2001 | Molin et al. | |
| 2002/0002389 A1 | 1/2002 | Bradley et al. | |

FOREIGN PATENT DOCUMENTS

| | | |
|---|---|---|
| WO | WO 94/06513 | 3/1994 |
| WO | WO 00/78391 | 12/2000 |
| WO | WO 03/051457 | 6/2003 |
| WO | WO 03/051457 A1 * | 6/2003 |
| WO | WO 2004/050177 | 6/2004 |

* cited by examiner

*Primary Examiner*—Carl H. Layno
*Assistant Examiner*—Brian T Gedeon
(74) *Attorney, Agent, or Firm*—Hahn Loeser & Parks, LLP; David J. Muzilla

(57) ABSTRACT

Certain embodiments of the present invention disclose an implant with electrode line connections for the connection of intracardial and/or epicardial electrode lines, wherein the electrode line connections have together at least three electrical contacts of which at least one is associated with a right-ventricular electrode and another is associated with a left-ventricular electrode, an impedance determining unit (IMP) which has a current or voltage source (I) and a measuring device (U) for a corresponding voltage or current measurement operation, which is connected to the electrical contacts and possibly a housing electrode of the implant, in such a way as to afford a tri- or quadrupolar impedance measuring arrangement which includes exclusively ventricular electrodes and in addition possibly the housing electrode, wherein the impedance measuring arrangement produces impedance measurement values and is connected to an evaluation unit (EVAL) and the evaluation unit (EVAL) is adapted to ascertain a minimum of the impedance measurement values within a first time window (defined relative to a ventricular event) as end-diastolic impedance (EDZ) and a maximum of the impedance measurement values within a second time window as end-systolic impedance (ESZ).

18 Claims, 5 Drawing Sheets

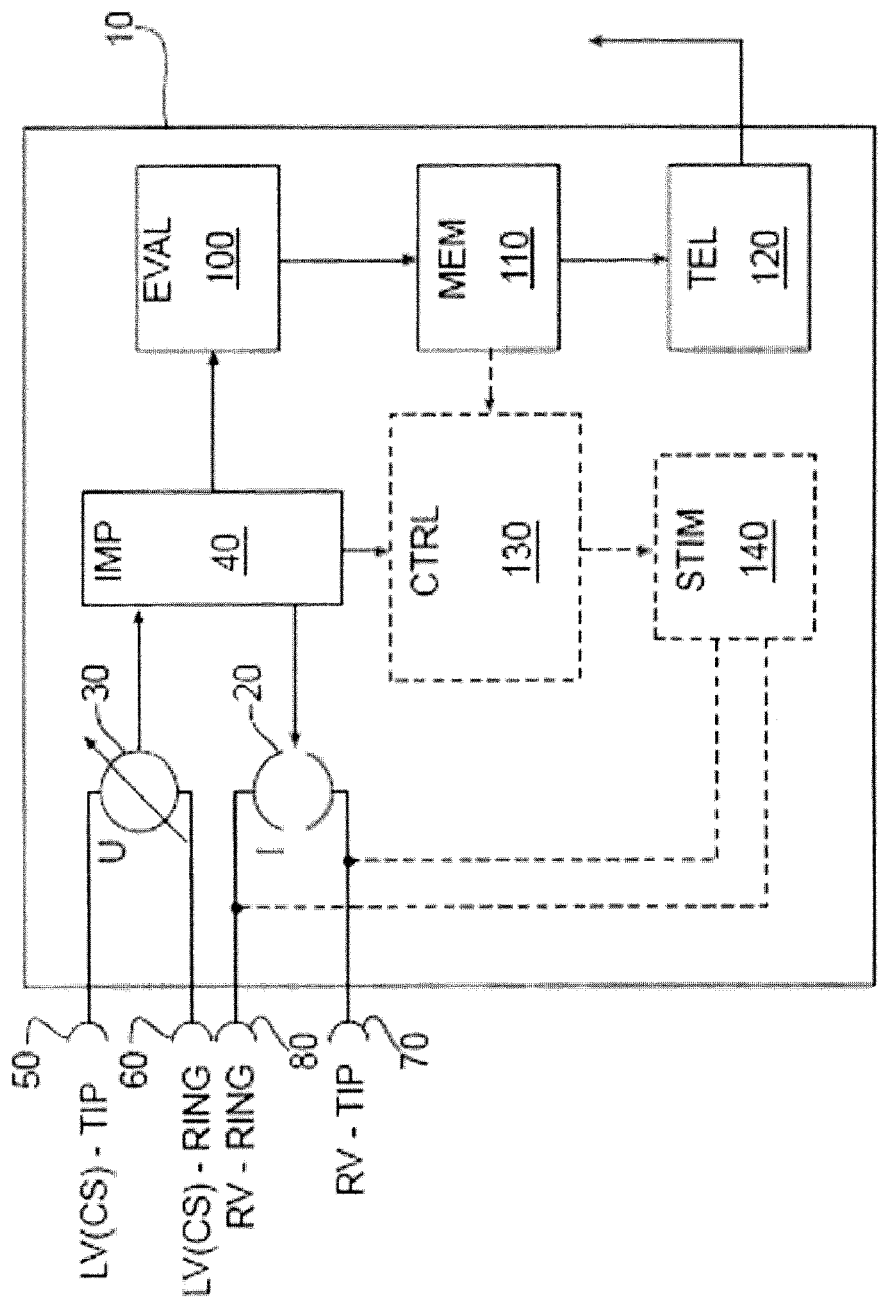

INTRACARDIAL IMPEDANCE MEASURING ARRANGEMENT

CROSS-REFERENCE TO RELATED APPLICATIONS/INCORPORATION BY REFERENCE

This application claims priority to German patent application Ser. No. 103 40 894.0 filed on Sep. 1, 2003.

This application also claims priority to German patent application Ser. No. 103 61 143.6 filed on Dec. 16, 2003.

TECHNICAL FIELD

Embodiments of the present invention relate to cardiac implants. In particular, certain embodiments of the present invention concern an implant with electrode line connections for the connection of intracardial and/or epicardial electrode lines, wherein the electrode line connections have together at least three electrical contacts of which at least one is associated with a right-ventricular electrode and another is associated with a left-ventricular electrode. The implant has an impedance measuring unit which has a current or voltage source and a measuring device for a corresponding voltage or current measurement operation, which is connected to the electrical contacts and possibly a housing electrode of the implant, in such a way as to afford a tri- or quadrupolar impedance measuring arrangement.

BACKGROUND OF THE INVENTION

Certain implants are known in the form of cardiac pacemakers, for example from WO 00/78391 or U.S. Ser. No. 2001/0012953.

Hemodynamic parameters are ascertained at present by means of echocardiography, by way of thorax impedance cardiography, by means of thermodilution catheters or with invasive pressure measurement procedures during electrophysiological investigations. Those processes require a high level of clinical complication and expenditure. For research purposes, pacemakers are sometimes implanted, which implement ventricular pressure measurement procedures by means of a sensor which is integrated into a stimulation electrode line. That means that special electrode lines are required for such a device.

SUMMARY OF THE INVENTION

There is still a need for an implant which permits improved detection and utilization of impedance values. In accordance with various embodiments of the present invention, such an implant is achieved with an implant of the kind set forth in the opening part of this specification, in which the impedance measuring arrangement includes exclusively ventricular electrodes and in addition possibly the housing electrode, wherein the impedance measuring arrangement produces impedance measurement values and is connected to an evaluation unit and the evaluation unit is adapted to ascertain a minimum of the impedance measurement values within a first time window (defined relative to a ventricular event) as end-diastolic impedance (EDZ) and a maximum of the impedance measurement values within a second time window as end-systolic impedance (ESZ).

An implant of that nature advantageously makes it possible by means of impedance measurement to ascertain hemodynamic parameters such as for example the beat volume.

Hemodynamic parameters of the blood circulation, in particular the beat volume (SV), the end-diastolic volume (EDV), the end-systolic volume (ESV) or the contractility of the heart as well as the dimensions of the ventricle afford important items of information about the condition of the cardiovascular system. Electrotherapy for the heart by means of implants can be improved by a sensor which detects hemodynamic and geometrical parameters.

Continuous monitoring of patients can be achieved by hemodynamic or geometrical data being communicated telemetrically for the purposes of home monitoring. Particularly for patients who suffer from a heart failure, observation of the hemodynamic condition is essential, in particular observation of the progress of (or improvement in) the illness or monitoring of the condition of the patient in the context of a resynchronization or medication therapy.

In accordance with various embodiments of the present invention, the intracardial impedance measuring apparatus includes an electrotherapeutic implant, for example an implantable pacemaker or cardioverter/defibrillator, which has a measuring device for determining an intracardial impedance or an intracardial impedance variation (impedance signal). The electrodes of the implant are preferably arranged in three or four chambers of the heart so that the arrangement is also suitable for multi-chamber stimulation and/or defibrillation. At least one bipolar electrode should be suitable for being arranged in the right ventricle (RV) and a second bipolar electrode in the proximity of the left ventricle (LV), more specifically either by virtue of arrangement in a lateral vein branching from the coronary sinus, or on the epicardium. The left-ventricular electrode is thus a coronary sinus electrode or an epicardial electrode.

The first and the second time windows are preferably shorter than a respective cardiac cycle interval and oriented relative to a ventricular event in a cardiac cycle. Two equally advantageous embodiments are discussed in this respect:

In a first embodiment, a first time window begins at a first initial time (X1) prior to the respective ventricular event and ends at a first end time (X2) after the ventricular event while a second time interval begins at a second initial time (Y1) after the ventricular event and ends at a second end time (Y2) after the ventricular event. In an alternative embodiment, the first initial time (X1) can also be after the respective ventricular event. The reference time selected for the second initial time (Y1) and the second end time (Y2) can also be a subsequent ventricular event.

The evaluation unit may be adapted to ascertain a beat impedance (SZ) representing a beat volume from a difference of the end-diastolic impedance (EDZ) and the end-systolic impedance (ESZ).

Alternatively, or in addition, the evaluation unit may be adapted to ascertain an EF parameter representing an ejection fraction (EF) from the beat impedance (SZ) and the end-diastolic impedance (EDZ). Instead of the end-diastolic impedance EDZ and the end-systolic impedance ESZ, it is also possible to evaluate the reciprocals thereof, namely the end-diastolic conductivity EDC (EDC=1/EDZ) and the end-systolic conductivity ESC (ESC=1/ESZ). The ejection fraction EF =SV/EDV is then approximately proportional to (EDC−ESC)/EDC.

Equally, an alternative embodiment can advantageously be implemented in which the evaluation unit is adapted to determine an impedance signal resulting from a time variation in the impedance measurement values and to ascertain from the first or second derivative of the impedance signal a contractility parameter representing a contractility of a heart.

The last-mentioned three hemodynamic parameters are of particular interest to the physician. Basically any kind of implant which makes it possible to ascertain hemodynamic parameters of interest by means of impedance measurement is advantageous.

In accordance with an embodiment of the present invention, the implant has a memory for one or more of the values in respect of beat impedance, the EF parameter, or contractility. In this connection the evaluation unit may be adapted to store the values in respect of beat impedance, end-diastolic impedance (EDZ), EF parameter and/or contractility at regularly recurring storage times.

It is a particularly attractive proposition if the evaluation unit is adapted, for a period between two successive storage times, to form mean values in respect of beat impedance, end-diastolic impedance (EDZ), EF parameter and/or contractility and to store one or more of the mean values.

In addition the evaluation unit may be adapted, from the development in respect of time of beat impedance, end-diastolic impedance (EDZ), EF parameter or contractility, to ascertain a respective trend value in respect of one or more of the parameters. Such trend values may also be stored at a respective storage time by the evaluation unit, in the memory, in accordance with an embodiment of the present invention.

In accordance with an embodiment of the present invention, the implant includes a telemetry unit which includes at least one telemetry transmitter and is connected to the memory and is adapted in response to an enquiry or at regular transmission times to send values in respect of beat impedance, end-diastolic impedance (EDZ), EF parameter, contractility or one or more mean or trend values to an external unit.

Moreover the implant may include all known and advantageous features of a cardiac pacemaker, cardioverter and/or defibrillator. Such features include in particular at least one ventricular or atrial stimulation unit as well as a control unit with which stimulation parameters such as for example the stimulation pulse strength, a stimulation frequency or the like can be adjusted. Such an implant may be in the form of a rate-variable cardiac pacemaker having a sensor for the physiological demand of a patient, by means of which the stimulation rate is to be adapted automatically by the implant to the physiological demand of a patient.

Further alternative embodiments are set forth by way of example in the description hereinafter.

In a first alternative embodiment, the implant includes an evaluation unit which is adapted to determine the changes in the left-ventricular diameter. Optionally, the evaluation unit can also be adapted to ascertain hemodynamic parameters of other heart chambers by way of impedance measurement. It is an important advantage of the invention that, for impedance measurement, the intracardial impedance measuring arrangement only requires conventional stimulation or defibrillation electrode lines.

It has been found that a quadrupolar impedance measuring arrangement with two electrodes in the right ventricle for the current feed and two further electrodes in the coronary sinus, which are associated with the left ventricle, are particularly advantageous and not susceptible to trouble, for measurement of a voltage resulting from the current which is introduced. Accordingly, a second alternative embodiment includes an implant which has a quadrupolar impedance measuring arrangement which is adapted for connecting two right-ventricular electrodes for the current feed and two left-ventricular electrodes arranged in a lateral vein branching from the coronary sinus, for measuring the voltage resulting from the current which is fed in.

BRIEF DESCRIPTION OF SEVERAL VIEWS OF THE DRAWINGS

The invention will now be described in greater detail by means of embodiments by way of example with reference to accompanying Figures in which:

FIGS. 1a and 1b shows two diagrammatic views of two very similar alternative configurations of an implant, in accordance with various embodiments of the present invention.

DETAILED DESCRIPTION OF THE INVENTION

Figure 1B:
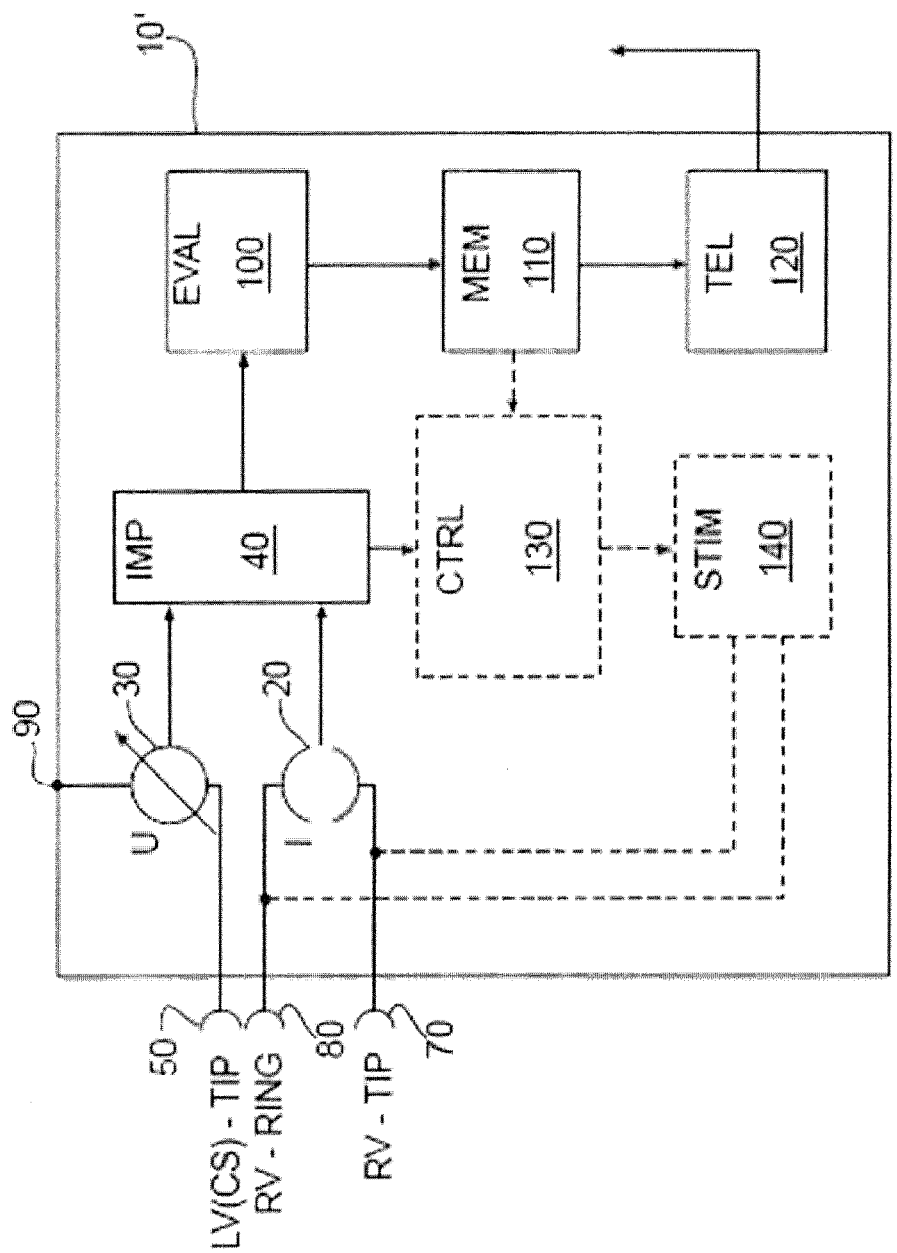

FIGS. 1a and 1b are diagrammatic views showing an implant 10 and 10' respectively with an impedance measuring arrangement which has a current source 20 (I) and a voltage measuring unit 30 (U) as well as an impedance determining unit 40 (IMP).

In the configuration shown in FIG. 1a, the voltage measuring unit 30 (U) is connected to a left-ventricular tip electrode 50 arranged in a lateral vein branching from the coronary sinus and a left-ventricular ring electrode 60 also arranged in a lateral vein branching from the coronary sinus. The current feed unit 20 (I) is connected to a right-ventricular tip 70 and a right-ventricular ring electrode 80—or more precisely, to contacts for the connection of those electrodes.

In the alternative configuration shown in FIG. 1b, the voltage measuring unit 30 (U) is connected on the one hand, as in FIG. 1a, to a left-ventricular tip electrode 50 and on the other hand, as a departure from FIG. 1a, to the implant housing 90 as a fourth electrode.

The impedance determining unit 40 (IMP) is connected both to the current feed unit 20 (I) and also to the voltage measuring unit 30 (U), for determining impedance. The respectively ascertained impedance value is transmitted on the part of the impedance determining unit 40 (IMP) to an evaluation unit 100 (EVAL). The evaluation unit 100 (EVAL) determines an end-diastolic impedance EDZ and an end-systolic impedance ESZ in the manner described hereinafter, from the values ascertained by the impedance determining unit 40 (IMP).

In addition, the evaluation unit 100 (EVAL) derives from those values a beat impedance SZ as the difference of an end-systolic impedance and an end-diastolic impedance (SZ=ESZ−EDZ), that is implemented in conjunction with a plausibility check, during which a check is made to ascertain whether the end-diastolic impedance (EDZ) is less than the end-systolic impedance (ESZ).

Further values ascertained by the evaluation unit EVAL, for each cardiac cycle, are an ejection fraction (EF) which is to be formed from the beat impedance and the end-diastolic impedance (EF~SZ*EDZ, as EF=SV/EDV and SV~SZ and EDV~1/EDZ) and the end-diastolic conductivity (EDC) and the end-systolic conductivity (ESC), as well as a contractility parameter representative of a contractility of a heart. All those values are stored by the evaluation unit 100 (EVAL) in a memory 110 (MEM) and more specifically at regularly recurring storage times, in accordance with an embodiment of the present invention.

The evaluation unit 100 (EVAL) is further adapted to form mean values in respect of beat impedance, the EF parameter or contractility for a respective period of time between two storage times, and also to store those mean values in the memory.

The evaluation unit 100 (EVAL) is further adapted to determine trends in respect of the parameters ascertained by the evaluation unit 100 (EVAL) and to store corresponding trend values in the memory 110 (MEM).

The memory 110 (MEM) is connected on the output side to a telemetry unit 120 (TEL) which is so designed that the values respectively stored in the memory are emitted at a regularly recurring transmission time from the telemetry unit by means of a transmitter unit associated with the telemetry unit, in such a way that the corresponding values can be received by an external unit and forwarded for example to a service center, a physician or the like.

Shown in broken line are examples of conventional component parts of an implant of that nature, namely a control unit 130 (CTRL) which is connected to the impedance determining unit 40 (IMP) and controls a stimulation unit 140 (STIM). In the illustrated example the stimulation unit 140 (STIM) is a right-ventricular stimulation unit and is thus connected to the connection for the right-ventricular ring electrode 80 and the right-ventricular tip electrode 70.

For impedance measurement the impedance measuring unit injects a below-threshold current between two electrodes of the electrode lines connected to the implant and/or the implant housing. The current is in the form of biphase pulses of constant amplitude. The voltage drop produced by the current (the voltage) is measured by way of another pair of the available electrodes. The measured voltage is proportional to the impedance of the tissue which is in the measuring region. In an alternative configuration the current-injecting electrodes and the electrodes for voltage measurement can be the same electrodes.

The measured voltage is firstly amplified and filtered by means of a programmable filter arrangement before it is subjected to analog/digital conversion. The programmable filter can be a low pass filter, a high pass filter or a band filter. In the embodiment described by way of example hereinafter the filter is a low pass filter. As described hereinbefore the measuring electrode arrangement may be quadrupolar in order to detect, in particular, changes in diameter of the ventricle by means of impedance measurement. Accordingly, the current is injected by way of two electrodes and the voltage measured by way of two other electrodes which are different from the current-injecting electrodes.

Figure 2A:
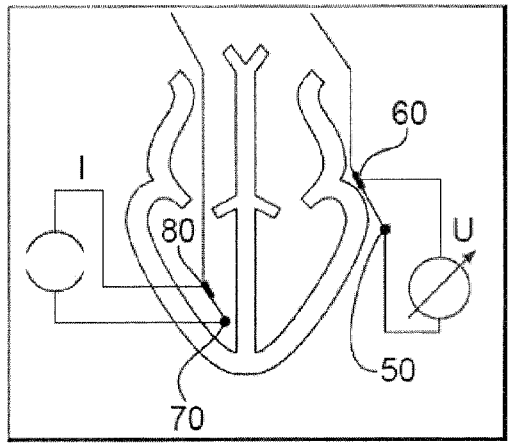
FIGS. 2a and 2b show two measuring configurations for determination of the left ventricle, in accordance with various embodiments of the present invention.

Of the various possible configurations, two configurations are particularly described for measurement in the left ventricle:

1. The current for impedance measurement is introduced between a right-ventricular tip electrode 70 and a right-ventricular ring electrode 80. The voltage resulting therefrom is measured between a left-ventricular tip electrode 50 and a left-ventricular ring electrode 60. In this case, the left-ventricular electrodes may be disposed in a lateral vein branching from the coronary sinus or arranged epicardially (see FIG. 2a).

Figure 2B:
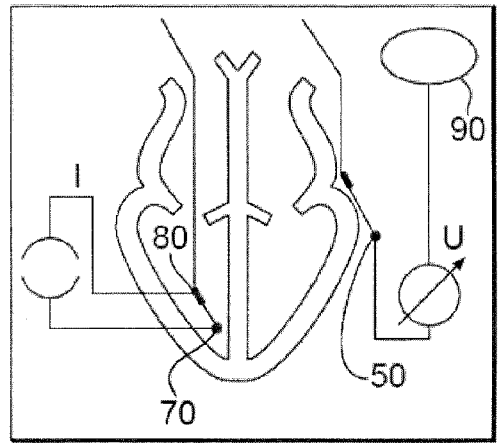

2. Alternatively the feed-in of current is also effected by way of the right-ventricular tip electrode 70 and the right-ventricular ring electrode 80, but voltage measurement is between a left-ventricular tip electrode 50 and the implant housing 90 (see FIG. 2b).

The impedance signal, which is measured with those configurations, depends in cubic relationship on the spacing between the two electrode lines. For a dipole field in a homogenous medium the following applies: $1/Z \approx d^3$, wherein Z is the impedance and d is the spacing between the electrode lines. Accordingly, the reciprocal of the impedance is an indirect measurement in respect of the left-ventricular volume because the left-ventricular volume is approximately proportional to the third power of the left-ventricular diameter. This is based on the assumption that the spacing "a" of the two electrodes of a current-feed dipole relative to each other is very much less than the spacing "d" of the voltage measuring electrode or electrodes from the current-feed dipole.

Figure 3:
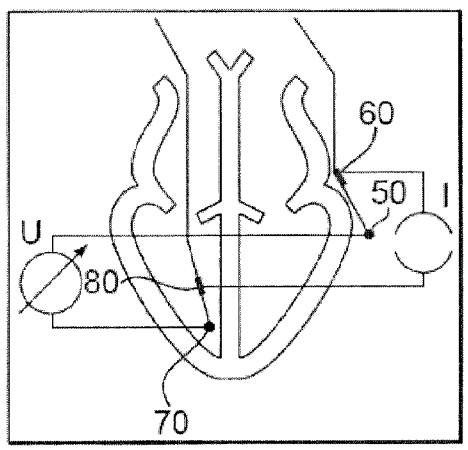
FIG. 3 shows an alternative impedance measurement configuration for the left ventricle, in accordance with an embodiment of the present invention.
Figure 4:
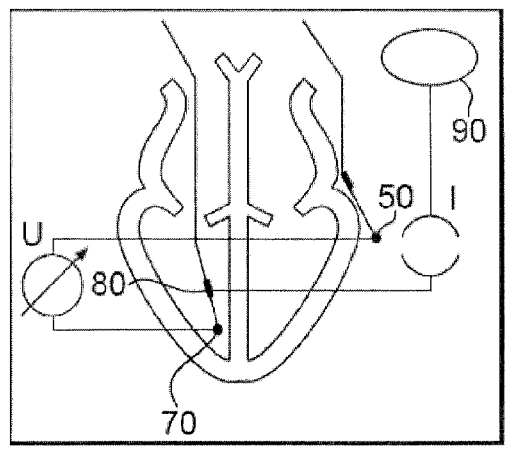
FIG. 4 shows a further alternative of an impedance measuring arrangement for the left ventricle, in accordance with an embodiment of the present invention.

Two alternative electrode configurations include:

3. A current feed-in between a right-ventricular ring electrode 80 and a left-ventricular ring electrode 60 and voltage measurement between a right-ventricular tip electrode 70 and a left-ventricular tip electrode 50 (see FIG. 3); or 4. A current feed-in between a right-ventricular ring electrode 80 and an implant housing 90 and voltage measurement between a right-ventricular tip electrode 70 and a left-ventricular tip electrode 50 (see FIG. 4).

In such arrangements, the reciprocal of the impedance corresponds to the spacing between the electrode lines if—as provided in configurations 3 and 4—"a" is very much less than "d".

Above-mentioned configurations 2 (see FIG. 2b) and 4 (see FIG. 4) present themselves when only one unipolar left-ventricular electrode line is available.

Evaluation of the impedance signal is effected by the evaluation unit 100 in the implant, being connected to the measuring unit. The evaluation unit is adapted to derive from the measured impedance signal parameters, in particular the variation in respect of time of impedance Z f(t) which depends on the end-diastolic and end-systolic diameters of the ventricle and thus the end-diastolic volume (EDV), the end-systolic volume (ESV) and the beat volume (SV) of the corresponding chamber. Evaluation applies in respect of relative values of those parameters and not the absolute values thereof.

The general concept on which determination of the relative volume is based relies on the differences in the spacings between right-ventricular and left-ventricular electrode lines during a contraction cycle. The ventricle expands during the diastole and reaches its maximum diameter at the end of that phase. Accordingly the impedance is minimal at the end of the diastole because the distance between the two electrode lines is at the maximum. The end-diastolic impedance is also referred to hereinafter as EDZ. On the other hand the impedance is at a maximum at the end of the systole because the spacing between the electrodes is at a minimum because of contraction of the ventricle. The corresponding end-systolic impedance is also referred to hereinafter as ESZ. The difference between the end-systolic impedance and the end-diastolic impedance is identified, as the beat impedance SZ, as follows: SZ=ESZ−EDZ. The beat impedance SZ is proportional to the beat volume SV of the ventricle. In addition the varying conductivities of the blood and the surrounding myocardium contribute to the change in the impedance signal. The conductivity of the blood is higher approximately by a factor of between 1.5 and 2 than the conductivity of the myocardium. The amount of blood in the measuring region is at a maximum during the end-diastolic phase and at a minimum during the end-systolic phase. That effect contributes to the changes in impedance, which are caused by the alternating ventricular diameter.

Figure 5:
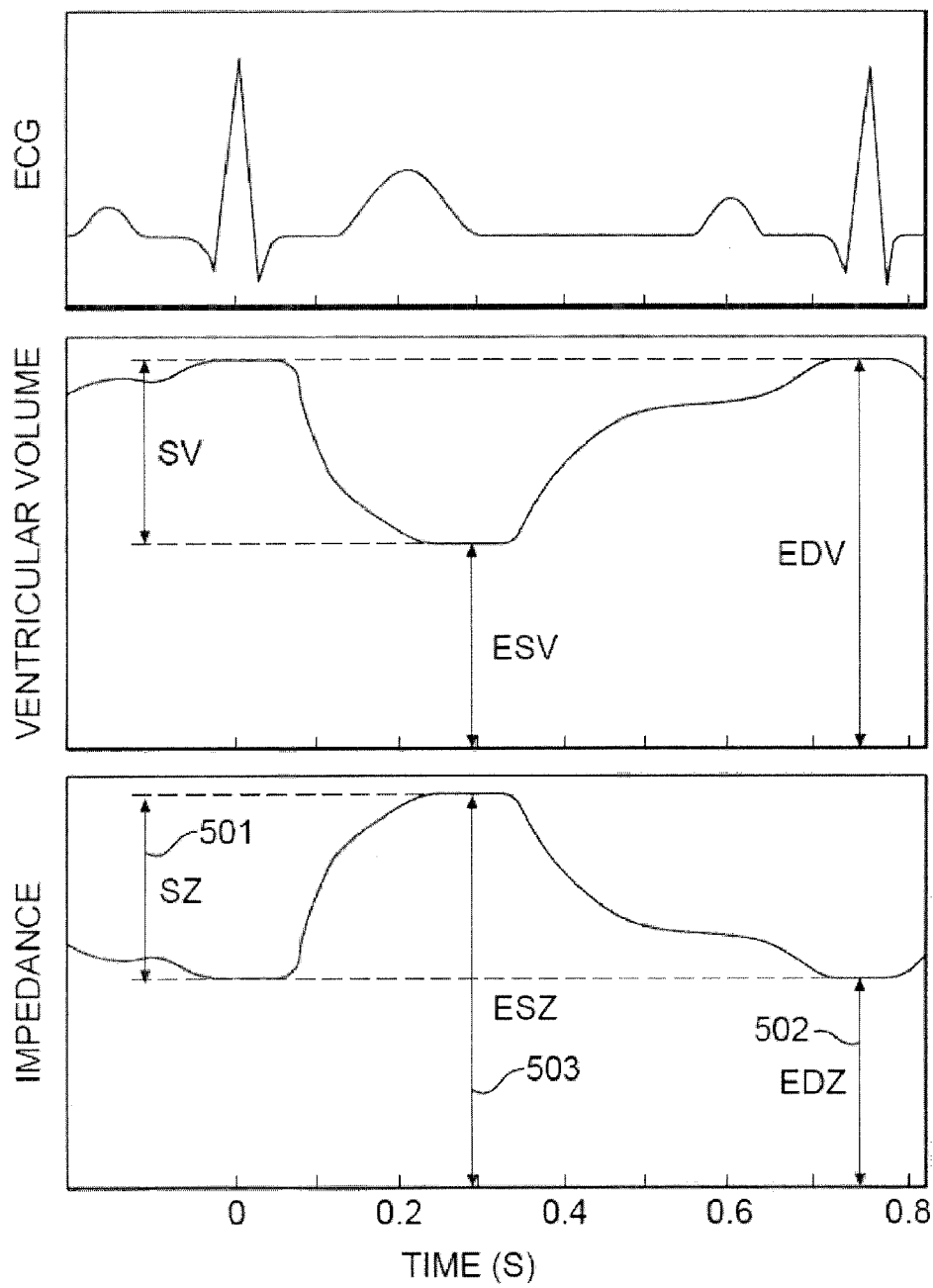
FIG. 5 shows an intracardial electrocardiogram, a representation of the ventricle volume and a representation of the resulting impedance in time association with each other, in accordance with an embodiment of the present invention.

FIG. 5 shows the ideal configuration of the impedance signal. In practice the signal will deviate from the ideal configuration because it is disturbed by other influences. A process for the processing of real impedance signals for extraction of the relevant parameters is part of the invention.

The process includes the following evaluation steps:

1. Measurement is triggered by a unique signal which characterizes the beginning of a cardiac cycle. A cardiac cycle begins with a ventricular contraction, that is to say with a ventricular event in an intracardial ECG and ends with the next following event. The triggering signal can either be derived directly from the ventricular intracardial electrocardiogram or alternatively or additionally it can be obtained by the marker channel of the implant. In this respect, the ventricular event is used to denote an electrical signal which involves or triggers a ventricular contraction. This may be a stimulation pulse of the pacemaker or an intrinsic, natural event. Such an intrinsic or natural event, as is known, is given by the QRS complex in an intracardial electrocardiogram.

2. The impedance signals of n successive cardiac cycles are ascertained in order to eliminate noise and respiration artifacts (i.e., signal components caused by respiration).

3. The end-diastolic impedance is determined as the minimum impedance Z of the averaged impedance signal within a predetermined time window which starts $x_1$ ms (ms=milliseconds) prior to the ventricular event and ends $x_2$ ms after the ventricular event. In that respect $x_1$ can be negative so that the time window can also start after the ventricular event. The end-systolic impedance is determined as the maximum value of the impedance Z of the averaged impedance signal during a second time window between $y_1$ ms and $Y_2$ ms after a ventricular event. In that respect, $y_1$ and $y_2$ can be negative values, that is to say the time window can also be determined relative to the next following ventricular event.

4. The beat impedance SZ 501 is calculated from the end-diastolic impedance EDZ 502 and the end-systolic impedance ESZ 503 (see FIG. 5). The sign of the beat impedance SZ 501 is subjected to a plausibility check, that is to say the end-diastolic impedance must be less than the end-systolic impedance. If that is not the case, for example by virtue of reversed measuring polarity, the sign is corrected.

Figure 6:
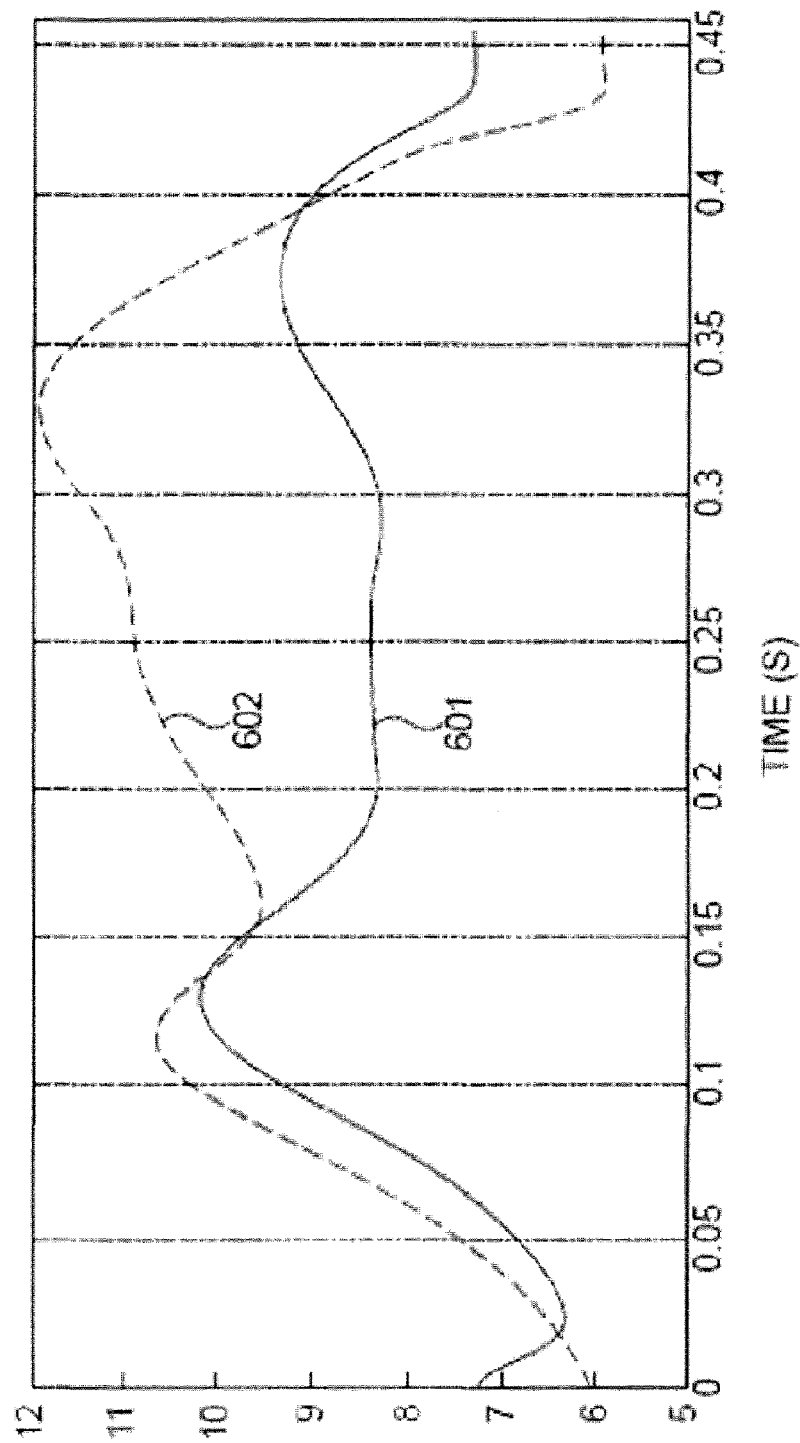
FIG. 6 shows an example of a measured impedance signal, in accordance with an embodiment of the present invention.

FIG. 6 shows an example of a measured impedance signal (601, 602). On the time scale here 0 ms corresponds to the point 50 ms prior to the R wave of the right-ventricular intracardial electrocardiogram in the case of a stimulus. The first maximum does not occur at the end of the systole but is caused by other influences. It should therefore not be within the systolic time window.

FIG. 6 shows two examples. In that respect, the solid line 601 corresponds to the rest condition of a patient and the broken line 602 corresponds to the condition when physical effort is involved. The physical effort results in an increased beat volume and thus an end-systolic impedance which is increased to 12 Ω.

As an alternative to the above-described process, the impedance signal can also be evaluated by calculation of the first and second derivatives. The maximum values (possibly within a predetermined time window) of the derivative of the reciprocal of the impedance correlates with the contractility of the ventricle.

For the purposes of determining stress-induced changes, signal evaluation is implemented in the context of long-term monitoring separately for the rest condition and for the stressed condition of the patient. It is possible in that way to ascertain long-term changes in respect of the beat volume and the end-diastolic volume or the contractility in the rest condition and in addition changes in the capacity for coping with stress. The rest condition and the stressed condition are distinguished by means of an accelerometer which is integrated into the implant, in accordance with an embodiment of the present invention. The accelerometer produces an acceleration signal corresponding to the acceleration of the accelerometer. If the acceleration signal as the output signal of the accelerometer exceeds a predetermined threshold value for a predetermined period of time, that is assessed as a stressed condition. If the amplitude of the acceleration signal remains below the threshold value for a predetermined period of time, that is assessed as a rest condition of the patient.

Further evaluations of the signal concern changes in the end-diastolic volume, the beat volume, the ejection fraction EF as a quotient of the beat volume and the end-diastolic volume: EF=SV/EDV, or contractility can be monitored in order to ascertain the hemodynamic condition of a patient, to observe the effect of a resynchronization therapy or medication -therapy or to ascertain given operating parameter settings of an implant and to optimize same. In addition the left-ventricular diameter can be observed in order to ascertain for example changes in the ventricle dimensions in the case of patients with dilated or hypertrophic cardiomyopathy.

There are various ways of supplying the physician with the relevant items of information:

1. Home Monitoring

Combined impedance parameters are communicated by means of a home monitoring long-distance telemetry procedure to a service center where the data are stored and trends computed. The combined impedance parameters can represent for example mean values over a respective period of 24 hours. Data transmission can be effected for example on a daily basis. In the service center, the diagnostic data are combined with other data from the implant, for example with the development in the heart rate, the counter conditions of various (event) counters and so forth. The trends can be communicated as cardio-reports by fax or the Internet to a responsible physician and can be inspected by him. In addition, alarms can be triggered if an unexpected configuration in respect of the hemodynamic values is detected.

2. Trend Recordings

The parameters extracted from the impedance signal are stored in the implant as long-term trends. Those trends can be for example queried and displayed on the occasion of a next following post-care examination. For the trend values to be stored, the impedance parameters are averaged, for example over 24 hours, so that long-term changes in hemodynamics are to be observed. Those changes can occur for example by virtue of remodeling as a consequence of a resynchronization therapy.

3. On-line Signal Transmission

The raw data of the impedance signal and the extracted parameters are transmitted from an implant to an external unit, for example a programming unit or another data recording unit by way of telemetry in an on-line mode. The data are displayed in real time and stored by the external unit. The physician can observe the hemodynamic changes as a consequence of certain intervention procedures such as for example various operating parameter adjustments for a cardiac pacemaker or cardioverter/defibrillator by means of the external unit.

Evaluation of the impedance signal can also include the following steps:

1. Parameter Optimization

Various operating parameters of the implant can be optimized by determining the hemodynamic condition. Examples in that respect are the AV-delay time, the VV-delay time or the stimulation mode of, for example, a biventricular pacemaker. That parameter optimization procedure can be effected interactively by a physician during a post-care investigation, or automatically by the implant. An example of continuous automatic parameter optimization is rate adaptation on the basis of the beat volume or the beat impedance.

2. Tachycardia Detection or Discrimination

In the case of an implantable cardioverter/defibrillator hemodynamic information is essential in order to confirm ventricular fibrillation or detect ventricular tachycardia. It is particularly important to differentiate (discriminate) hemodynamically stable and hemodynamically unstable ventricular tachycardias from each other in order to avoid unnecessary shock treatment. For that purpose a tachycardia episode is additionally ascertained by a hemodynamic sensor.

What is claimed is:

1. An implant comprising:
    electrode line connections for the connection of intracardial and/or epicardial electrode lines, wherein the electrode line connections have together at least three electrical contacts of which at least one is associated with a right-ventricular electrode and another is associated with a left-ventricular electrode;
    an impedance determining unit (IMP) which has a current or voltage source (I) and a measuring device (U) for a corresponding voltage or current measurement operation, which is connected to the electrical contacts and possibly a housing electrode of the implant, in such a way as to afford a tri- or quadrupolar impedance measuring arrangement which includes exclusively ventricular electrodes and in addition possibly the housing electrode,
    wherein the impedance measuring arrangement produces impedance measurement values and is connected to an evaluation unit (EVAL) and the evaluation unit (EVAL) is adapted to ascertain a minimum of the impedance measurement values within a first time window as end-diastolic impedance (EDZ) and a maximum of the impedance measurement values within a second time window as end-systolic impedance (ESZ), wherein said first and second time windows are each shorter than a complete cardiac cycle and are oriented relative to a ventricular event in a cardiac cycle, or to form an end-diastolic conductivity (EDC) as the reciprocal of the end-diastolic impedance (EDZ) and an end-systolic conductivity (ESC) as the reciprocal of the end-systolic impedance (ESZ),
    and wherein the evaluation unit is additionally adapted to determine an impedance signal resulting from a time variation in the impedance measurement values and to ascertain from a first or a second derivative of the impedance signal a contractility parameter representing a contractility of a heart.

2. The implant as set forth in claim 1 wherein the first time window begins at a first initial time (x1) prior to the respective ventricular event and ends at a first end time (x2) after said ventricular event while the second time interval begins at a second initial time (y1) after said ventricular event and ends at a second end time (y2) after the ventricular event.

3. The implant as set forth in claim 2 wherein the first initial time (x1) and the first end time (x2) of the first time window and also the second initial time (y1) and the second end time (y2) of the second time interval are prior to the ventricular event as a reference time.

4. The implant as set forth in claim 3 wherein the evaluation unit (EVAL) is adapted to ascertain a beat impedance (SZ) representing a beat volume from a difference of the end-diastolic impedance (EDZ) and the end-systolic impedance (ESZ).

5. The implant as set forth in claim 4 wherein the evaluation unit is adapted to ascertain an EF parameter representing an ejection fraction (EF) from the beat impedance (SZ) and the end-diastolic impedance (EDZ).

6. The implant as set forth in claim 5 further comprising a memory (MEM) for values in respect of beat impedance and/or the EF parameter and/or contractility and/or further values including that of impedance values and conductivity values.

7. The implant as set forth in claim 6 wherein the evaluation unit (EVAL) is adapted to store values in respect of beat impedance and/or the EF parameter and/or contractility at regularly recurring storage times.

8. The implant as set forth in claim 7 wherein the evaluation unit (EVAL) is adapted, for a period between two successive storage times, to form mean values in respect of beat impedance and/or EF parameter and/or contractility and to store the mean value or values.

9. The implant as set forth in claim 8 wherein the evaluation unit is adapted to ascertain from a development in respect of time of the beat impedance and/or the EF parameter and/or contractility, a trend value in respect of beat impedance and/or the EF parameter and/or contractility.

10. The implant as set forth in claim 9 wherein the evaluation unit (EVAL) is adapted to store the trend value or values at a respective storage time in the memory.

11. The implant as set forth in claim 10 further comprising a telemetry unit (TEL) which includes at least one telemetry transmitter and is connected to the memory and is adapted in response to an enquiry or at regular transmission times to send values in respect of beat impedance and/or EF parameter and/or contractility and/or one or more mean or trend values to an external unit.

12. The implant as set forth in claim 11 further comprising at least one control unit (CTRL) and stimulation unit (STIM) with which stimulation, cardioversion, and/or defibrillation pulses are produced and delivered to at least one of the electrode line connections.

13. The implant as set forth in claim 12 wherein said quadrupolar impedance measuring arrangement is adapted for connection to two right-ventricular electrodes for a current feed-in and two left-ventricular electrodes arranged in a coronary sinus for measuring a voltage resulting from the current which is fed in.

14. The implant as set forth in claim 5 wherein the evaluation unit (EVAL) is adapted to store values in respect of beat impedance and/or the EF parameter and/or contractility at regularly recurring storage times.

15. The implant as set forth in claim 6 wherein the evaluation unit (EVAL) is adapted, for a period between two successive storage times, to form mean values in respect of beat impedance and/or EF parameter and/or contractility and to store the mean value or values.

16. The implant as set forth in claim 6 further comprising a telemetry unit (TEL) which includes at least one telemetry transmitter and is connected to the memory and is adapted in response to an enquiry or at regular transmission times to send values in respect of beat impedance and/or EF parameter and/or contractility and/or one or more mean or trend values to an external unit.

17. The implant as set forth in claim 1 further comprising at least one control unit (CTRL) and stimulation unit (STIM) with which stimulation, cardioversion, and/or defibrillation pulses are produced and delivered to at least one of the electrode line connections.

18. The implant as set forth in claim 1 wherein said quadrupolar impedance measuring arrangement is adapted for connection to two right-ventricular electrodes for a current feed-in and two left-ventricular electrodes arranged in a coronary sinus for measuring a voltage resulting from the current which is fed in.

* * * * *